(12) United States Patent
Song

(10) Patent No.: US 8,840,675 B2
(45) Date of Patent: Sep. 23, 2014

(54) DURABLE RESURFACING HIP REPLACEMENT DEVICE

(75) Inventor: Benjamin Soo-il Song, Los Angeles, CA (US)

(73) Assignees: Benjamin S. Song, Los Angeles, CA (US); Jennifer J. Song, Los Angeles, CA (US); Angela Y. Song, Los Angeles, CA (US); Michael A. Song, Los Angeles, CA (US)

( * ) Notice: Subject to any disclaimer, the term of this patent is extended or adjusted under 35 U.S.C. 154(b) by 712 days.

(21) Appl. No.: 12/765,759

(22) Filed: Apr. 22, 2010

(65) Prior Publication Data
US 2011/0264233 A1   Oct. 27, 2011

(51) Int. Cl.
   A61F 2/32    (2006.01)
   A61F 2/36    (2006.01)
   A61B 17/74   (2006.01)
   A61F 2/30    (2006.01)
   A61F 2/46    (2006.01)

(52) U.S. Cl.
   CPC .............. *A61F 2/36* (2013.01); *A61F 2/30744* (2013.01); *A61F 2/3603* (2013.01); *A61F 2002/3686* (2013.01); *A61B 17/744* (2013.01); *A61F 2002/365* (2013.01); *A61F 2002/30448* (2013.01); *A61F 2002/30774* (2013.01); *A61F 2002/4635* (2013.01); *A61F 2002/368* (2013.01); *A61F 2002/30507* (2013.01); *A61F 2002/3085* (2013.01); *A61F 2002/3652* (2013.01); *A61F 2002/30405* (2013.01); *A61F 2002/3682* (2013.01); *A61F 2002/4631* (2013.01); *A61F 2002/3684* (2013.01); *A61F 2002/30331* (2013.01); *A61F 2002/3692* (2013.01)

USPC ...................................... 623/22.11; 623/23.15

(58) Field of Classification Search
   CPC .............. A61F 2/32; A61F 2/36; A61F 2002/368–2002/3686
   USPC ............ 623/23.15, 23.25, 23.26, 22.46, 623/19.11–19.14, 22.11, 22.41–22.45, 623/23.12, 23.27, 23.42, 23.44, 18.11, 623/22.15, 22.4, 23.11, 23.18, 23.39, 23.4
   See application file for complete search history.

(56) References Cited

U.S. PATENT DOCUMENTS

| | | | | |
|---|---|---|---|---|
| 5,370,706 A | * | 12/1994 | Bolesky et al. | 623/23.44 |
| 6,136,035 A | * | 10/2000 | Lob et al. | 623/23.15 |
| 6,616,697 B2 | * | 9/2003 | Sotereanos | 623/23.26 |
| 2007/0038306 A1 | * | 2/2007 | O'Gara | 623/22.42 |

* cited by examiner

*Primary Examiner* — Christopher D Prone
(74) *Attorney, Agent, or Firm* — John K. Park; Park Law Firm

(57) ABSTRACT

A minimal invasive hip arthroplasty device is provided. The device includes a long nail portion, a lag screw portion, distal locking screws, and a resurfacing head. The long nail portion is inserted into a shaft body of a femur from a top portion of the femur and disposed in the femur. The lag screw portion engages and anchors at the long nail portion through a lag screw hole, and the lag screw portion is inserted into a neck of the femur. The distal locking screws queue through the shaft body of the femur perpendicularly and fix the long nail portion to the femur further. The resurfacing head includes a cup portion configured to cover a head of the femur and a fixing pin portion configured to be inserted into the head and the neck of the femur and engaging the lag screw portion through a resurfacing head hole.

14 Claims, 8 Drawing Sheets

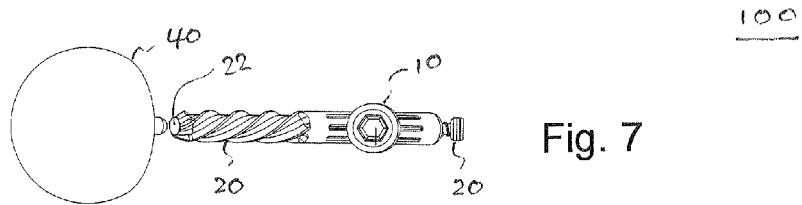
Fig. 6 Fig. 5 Fig. 8
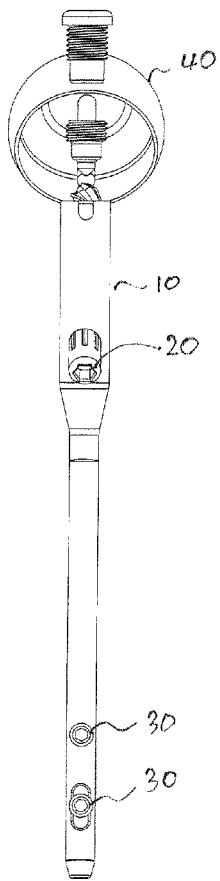 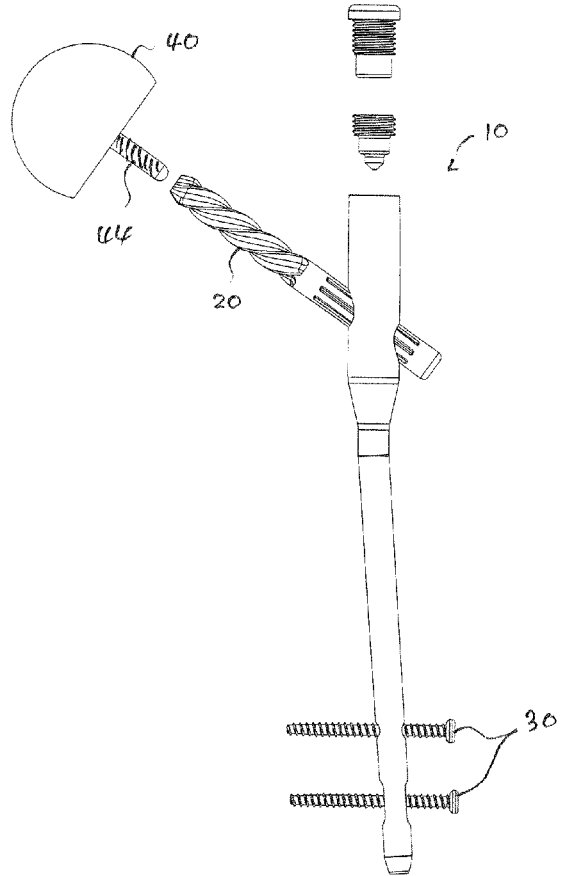 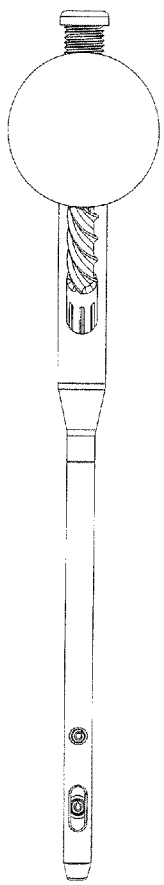
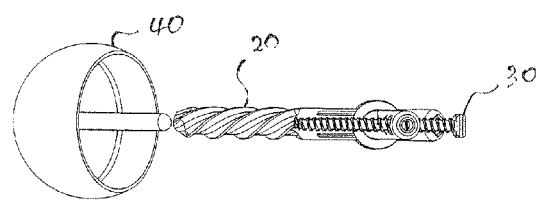
Fig. 9

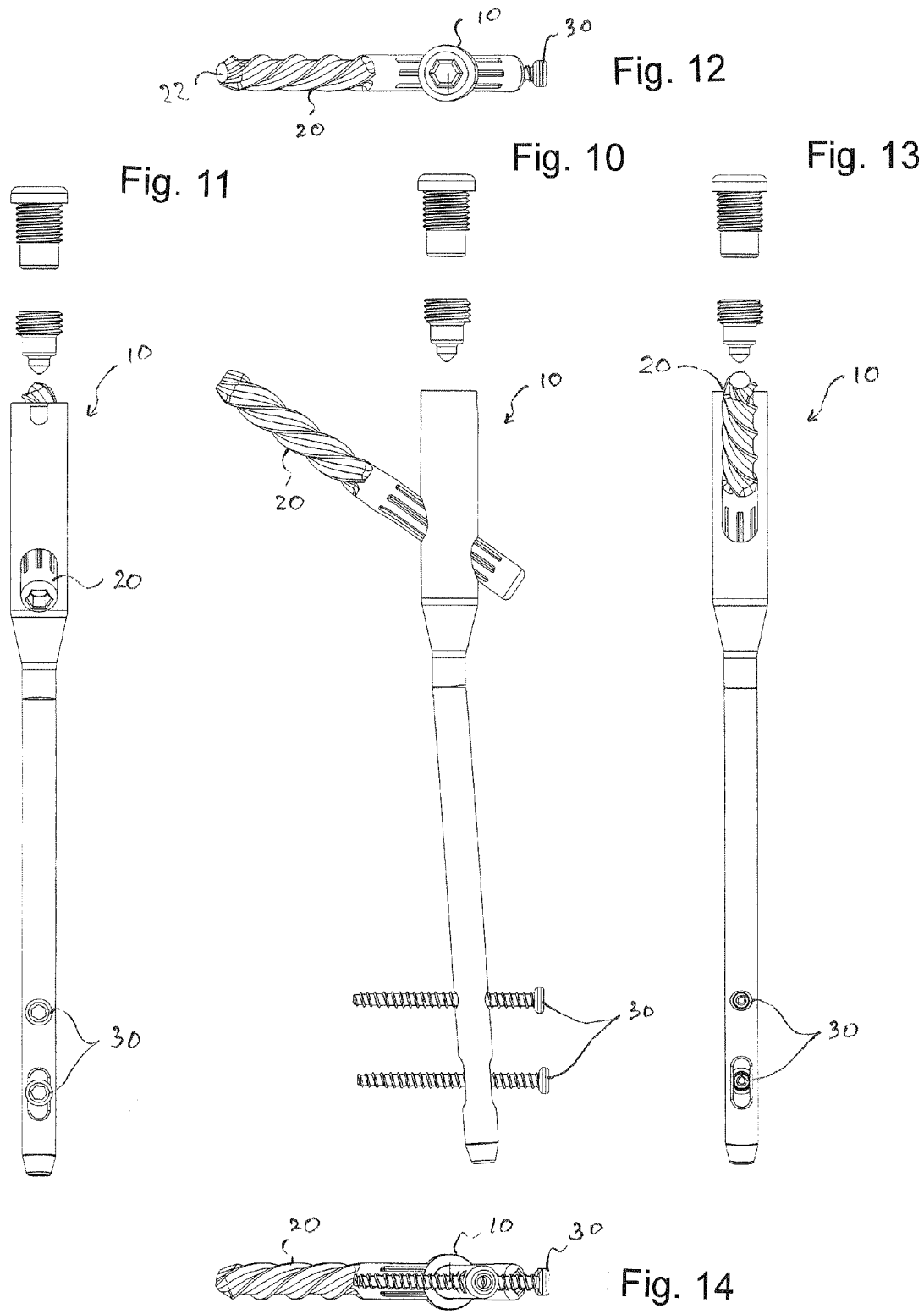

DURABLE RESURFACING HIP REPLACEMENT DEVICE

BACKGROUND OF THE INVENTION

The present invention relates to a minimal invasive hip arthroplasty device. More particularly, this invention relates to a minimal invasive hip arthroplasty device, which provides a lasting solution to patients with end stage arthritis of hip.

Joint replacement may provide a dramatic improvement in the quality of life of patients with end stage of arthritis of the hip. However, those who are young and active still pose formidable problem, as conventional hip arthroplasty does not provide a lasting solution to their needs. As a less invasive method of joint reconstruction, variable resurfacing of the hip has been introduced. However, because of high technical difficulty and big complication rate, it has not been commonly used.

A new design for all age groups for arthritis of the hip joint is provided. This new hip arthroplasty design overcomes the difficult problems of both conventional total hip replacment (THR) and resrufacing prosthesis of the hip.

Accordingly, a need for a minimal invasive hip arthroplasty device has been present for a long time considering the expansive demands in the everyday life. This invention is directed to solve these problems and satisfy the long-felt need.

SUMMARY OF THE INVENTION

The present invention contrives to solve the disadvantages of the prior art.

An object of the invention is to provide a minimal invasive hip arthroplasty device.

Another object of the invention is to provide a minimal invasive hip arthroplasty device, which provides a long-lasting solution to arthritis.

Still another object of the invention is to provide a minimal invasive hip arthroplasty device, which overcomes problems in resurfacing prosthesis of hip.

An aspect of the invention provides a minimal invasive hip arthroplasty device.

The minimal invasive hip arthroplasty device comprises a long nail portion, a lag screw portion, one or more distal locking screws, and a resurfacing head.

The long nail portion is configured to be inserted into a shaft body of a femur from a top portion of the femur and disposed in the femur.

The lag screw portion engages and anchors at the long nail portion through a lag screw hole with an angle from about 110 degrees to about 140 degrees, and the lag screw portion is inserted into a neck of the femur.

The one or more distal locking screws are configured to queue through the shaft body of the femur perpendicularly and fix the long nail portion to the femur further.

The resurfacing head comprises a cup portion configured to cover a head of the femur and a fixing pin portion configured to be inserted into the head and the neck of the femur and engaging the lag screw portion through a resurfacing head hole to support the cup portion.

The lag screw hole may be provided obliquely through the long nail portion.

The long nail portion may be cylindrical and hollow, and the long nail portion may further comprise a set screw configured to engage threads provided inside the long nail portion.

The lag screw portion may comprise: a support portion configured to queue into the lag screw hole; a screw portion extending from the support portion; the resurfacing head hole provided through the screw portion; and a locking groove provided lengthwise along an outer surface of the support portion.

The set screw may be configured to proceed along the threads provided inside the long nail portion and lock into the locking groove of the lag screw portion so as to prevent from rotating and allowing the lag screw portion to slide along the lag screw hole.

The resurfacing head hole may comprise inner male threads configured to engage female threads provided on the fixing pin portion.

The long nail portion may further comprise one of more distal locking screw holes provided in a low portion of the long nail portion substantially perpendicularly to a direction of length of the long nail portion.

One of the one or more distal locking screw holes may have an oblong cross-section along the direction of length of the long nail portion so as to allow the distal locking screw to be adjusted upward or downward.

Each of the one or more distal locking screws may comprise a head portion and a male thread portion.

Each of the one or more distal locking screw holes may comprise inner female threads for engaging the male thread portion of the distal locking screw.

The long nail portion may further comprise an end cap configured to cap the top end option of the long nail portion.

The end cap may comprise a male thread portion configured to engage the inner female threads of the long nail portion.

The fixing pin portion of the resurfacing head may be fixed to the resurfacing head hole provided through the lag screw portion by means of adhesive or glue.

The fixing pin portion of the resurfacing head may be fixed to the resurfacing head hole provided through the lag screw portion by means of cement.

The long nail portion may be bent slightly by a predetermined angle in a middle portion. The predetermined angle may be determined by a general shape of the femur.

The resurfacing head may be configured to engage an acetabular cup embedded in a portion of pelvis.

The advantages of the present invention are: the minimal invasive hip arthroplasty device can provide:

(1) a long-lasting solution to arthritis;
(2) conservative on femoral side and less bleeding due to minimal invasive cutting to the femur;
(3) lower dislocation rate;
(4) increasing range of motion;
(5) gait analysis similar to normal hip;
(6) no burning bridges (simple future revision);
(7) technically east and accurate resurfacing of prosthetic fitting;
(8) easy changing neck-shaft angle without disturbing over all function;
(9) preventing femoral neck fracture which is a common complication in the conventional resurface replacement;
(10) ability to perform two procedures at the same time: arthroplasty and open reduction and internal fixation arthritis and fractured hip; and
(11) fast recovery.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein:

FIG. 5 is a perspective side view showing a minimal invasive hip arthroplasty device according to an embodiment of the present invention;

FIG. 6 is a perspective rear view of the minimal invasive hip arthroplasty device of FIG. 5;

FIG. 7 is a perspective top view of the minimal invasive hip arthroplasty device of FIG. 5;

FIG. 8 is a perspective front view of the minimal invasive hip arthroplasty device of FIG. 5;

FIG. 9 is perspective bottom view of the minimal invasive hip arthroplasty device with a partially cutout lag screw portion of FIG. 5;

FIG. 10 is a perspective side view of a long nail portion and a lag screw portion according to an embodiment of the present invention;

FIG. 11 is a perspective rear view of FIG. 10;

FIG. 12 is a perspective top view of FIG. 10;

FIG. 13 is a perspective front view of FIG. 10;

FIG. 14 is a perspective bottom view of FIG. 10 with a partially cut-out lag screw portion;

DETAILED DESCRIPTION EMBODIMENTS OF THE INVENTION

Figure 1:
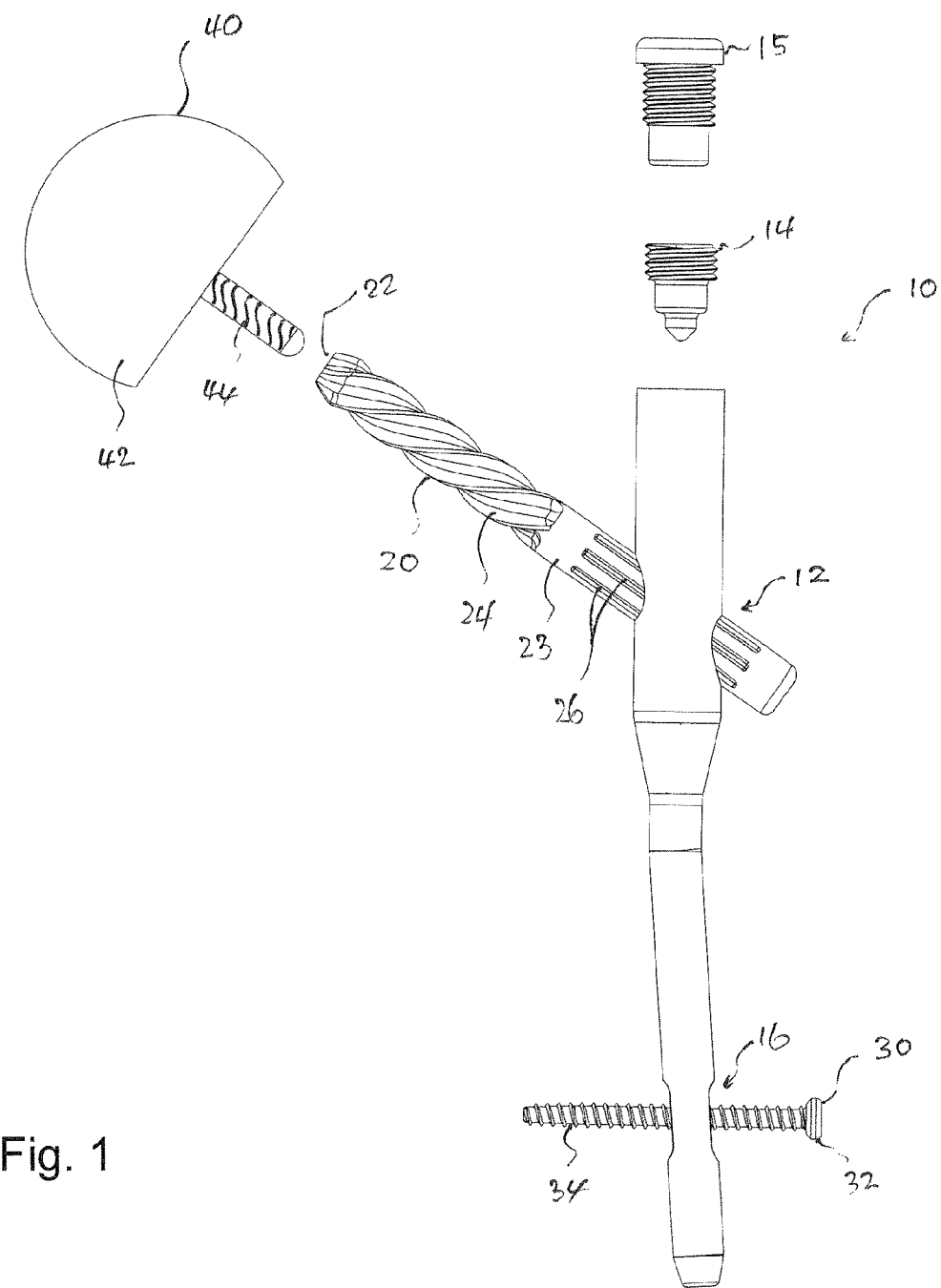
FIG. 1 is a side plan view showing a minimal invasive hip arthroplasty device according to an embodiment of the present invention.
Figure 2:
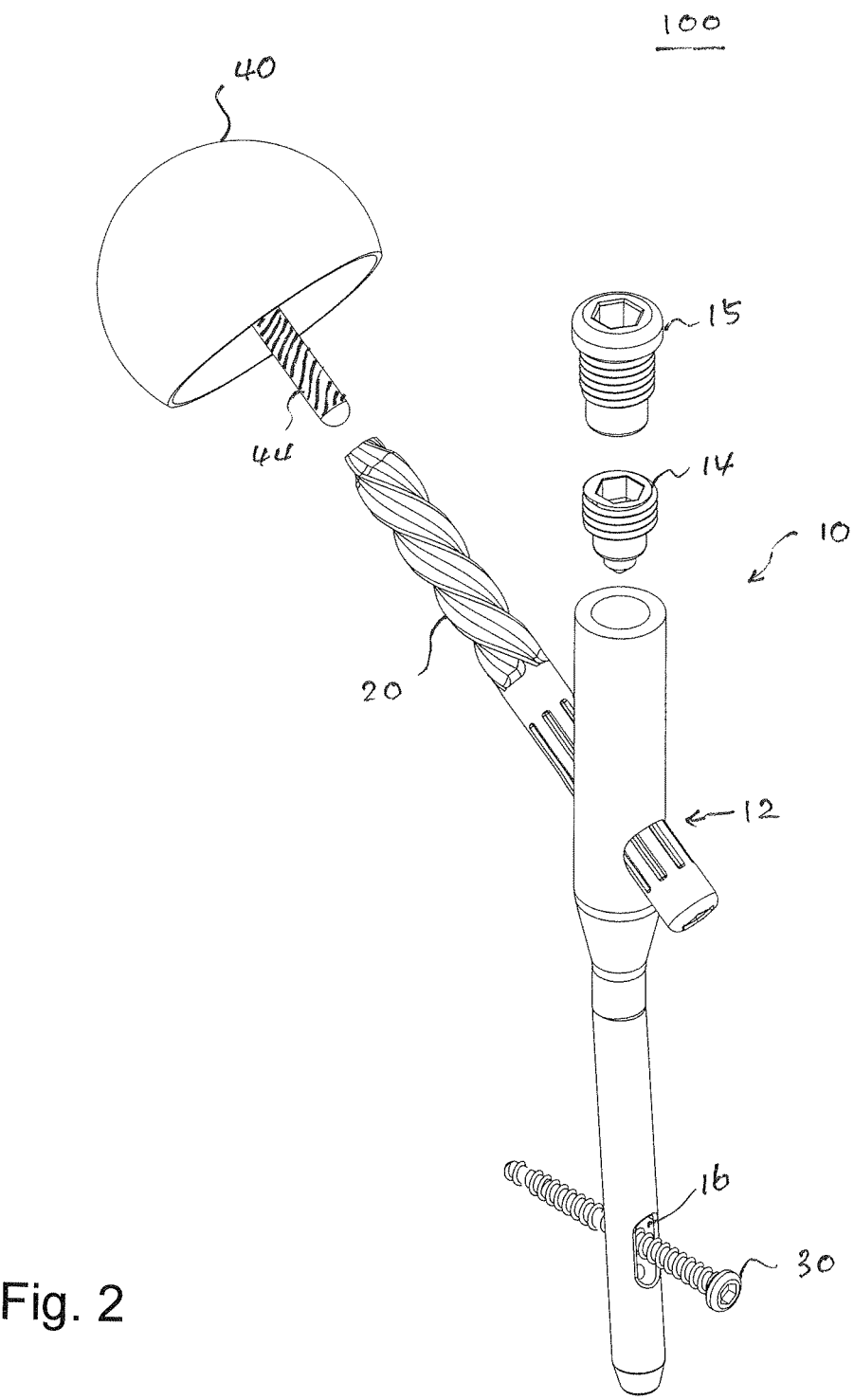
FIG. 2 is a perspective view showing the minimal invasive hip arthroplasty device FIG. 1.
Figure 3:
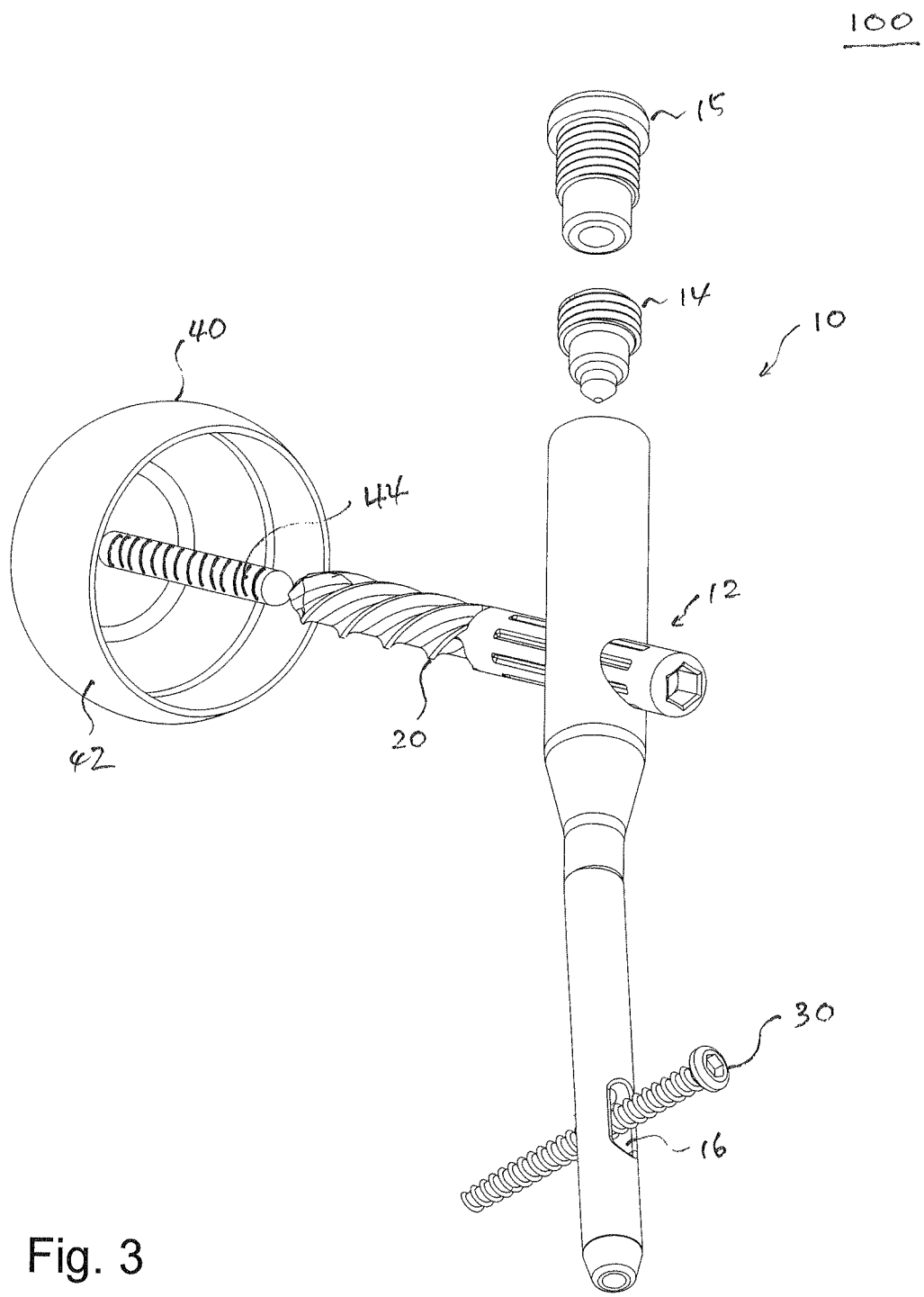
FIG. 3 is another perspective view showing the minimal invasive hip arthroplasty device FIG. 1.
Figure 4:
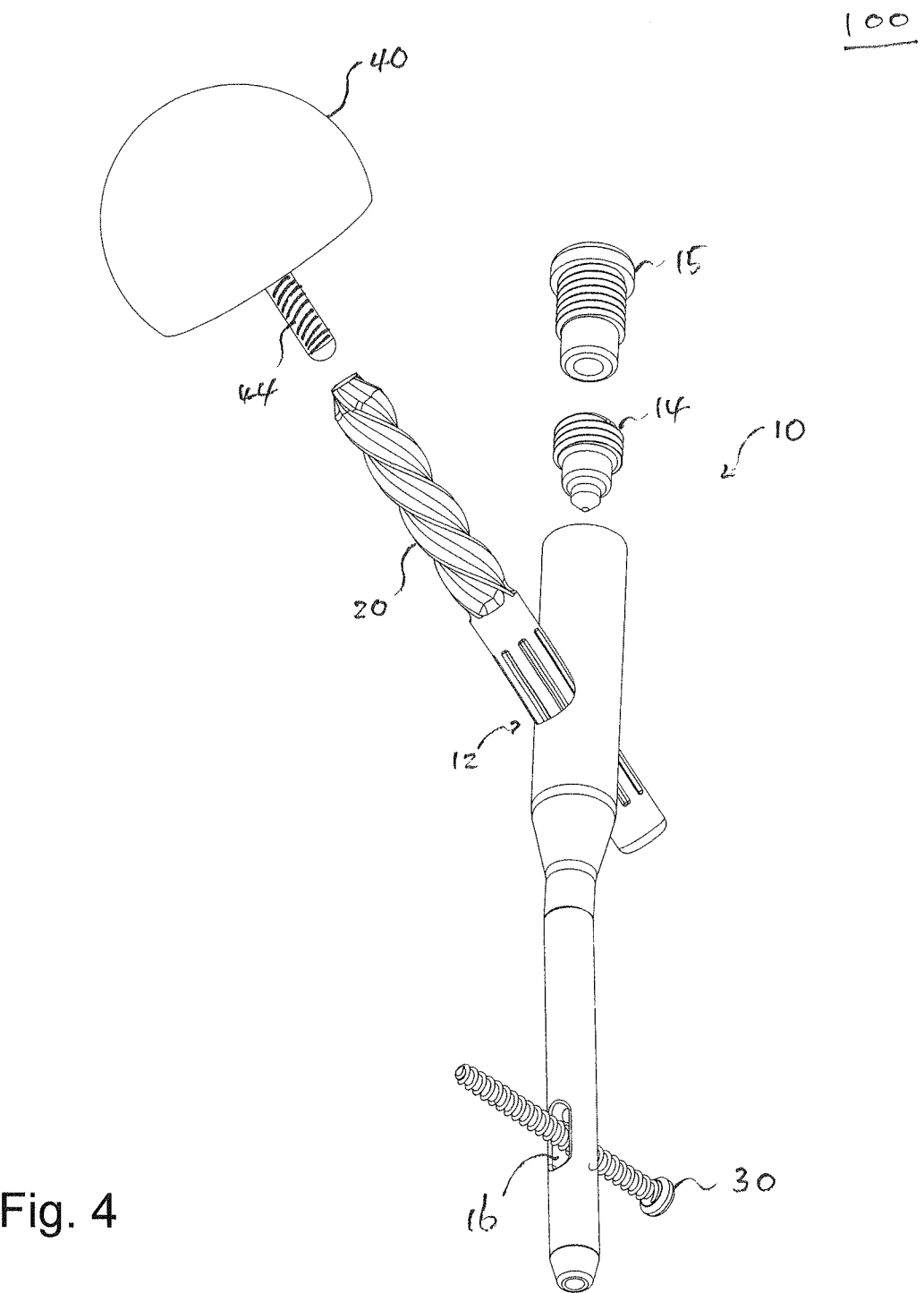
FIG. 4 is another perspective view showing the minimal invasive hip arthroplasty device FIG. 1.
Figure 15:
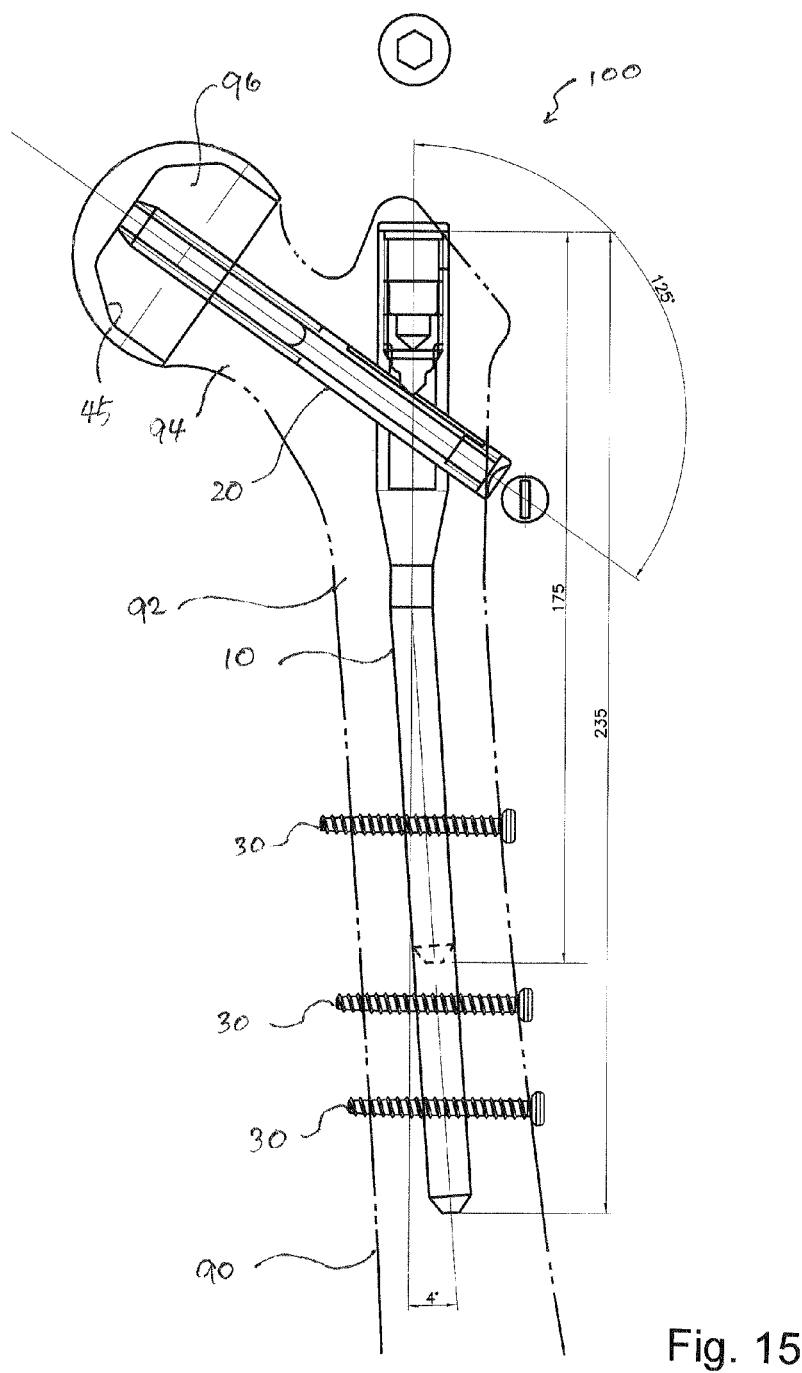
FIG. 15 is a perspective view showing a minimal invasive hip arthroplasty device installed in a femur according to an embodiment of the present invention.

FIGS. 1-4 show perspective views of a minimal invasive hip arthroplasty device 100 according to an embodiment of the present invention. FIGS. 5-9 show a minimal invasive hip arthroplasty device 100 according to another embodiment of the invention. FIGS. 10-14 show long nail portion and lag screw portion of a minimal invasive hip arthroplasty device 100 according to still another embodiment of the invention. FIG. 15 shows perspective view showing a minimal invasive hip arthroplasty device 100 according to still another embodiment of the invention installed in a femur.

An aspect of the invention provides a minimal invasive hip arthroplasty device 100.

The minimal invasive hip arthroplasty device 100 comprises a long nail portion 10, a lag screw portion 20, one or more distal locking screws 30, and a resurfacing head 40.

The long nail portion 10 is configured to be inserted into a shaft body 92 of a femur 90 from a top portion of the femur 90 and disposed in the femur 90 as shown in FIG. 15.

The lag screw portion 20 engages and anchors at the long nail portion 10 through a lag screw hole 12 with an angle from about 110 degrees to about 140 degrees, and the lag screw portion 20 is inserted into a neck 94 of the femur 90 as shown in FIG. 15.

The one or more distal locking screws 30 are configured to queue through the shaft body 92 of the femur 90 perpendicularly and fix the long nail portion 10 to the femur 90 further.

The resurfacing head 40 comprises a cup portion 42 configured to cover a head 96 of the femur 90 and a fixing pin portion 44 configured to be inserted into the head 96 and the neck 94 of the femur 90 and engaging the lag screw portion 20 through a resurfacing head hole 22 to support the cup portion 42.

Figure 16:
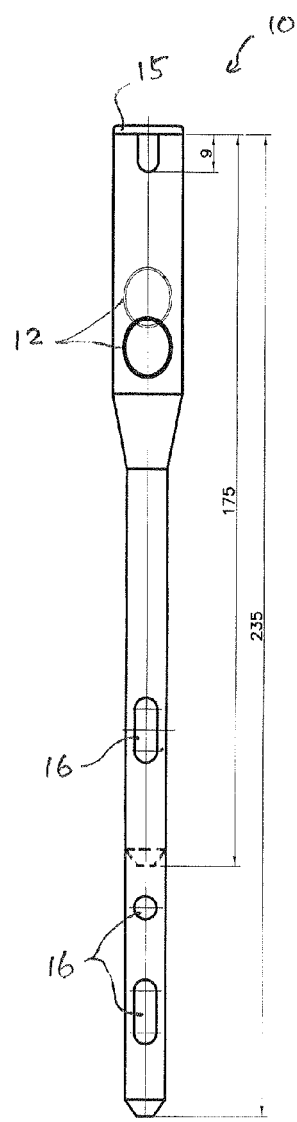
FIG. 16 is a front view of a long nail portion.

The lag screw hole 12 may be provided obliquely through the long nail portion 10 as shown in FIG. 16.

The long nail portion 10 may be cylindrical and hollow, and the long nail portion 10 may further comprise a set screw 14 configured to engage threads provided inside the long nail portion 10.

The lag screw portion 20 may comprise: a support portion 23 configured to queue into the lag screw hole 12; a screw portion 24 extending from the support portion 23; the resurfacing head hole 22 provided through the screw portion 24; and a locking groove 26 provided lengthwise along an outer surface of the support portion 23.

The set screw 14 may be configured to proceed along the threads provided inside the long nail portion 10 and lock into the locking groove 26 of the lag screw portion 20 so as to prevent from rotating and allowing the lag screw portion 20 to slide along the lag screw hole 12.

The resurfacing head hole 22 may comprise inner female threads configured to engage male threads provided on outer surface of the fixing pin portion 44.

In certain embodiment of the invention, the fixing pin portion 44 may be fixed to the resurfacing head hole 22 by means of adhesive or glue without any threads on the fixing pin portion 44, in which the resurfacing head 40 may be fixed without rotating in case of threads related.

The long nail portion 10 may further comprise one of more distal locking screw holes 16 provided in a low portion of the long nail portion 10 substantially perpendicularly to a direction of length of the long nail portion 10 as shown in FIG. 16.

One of the one or more distal locking screw holes 16 may have an oblong cross-section along the direction of length of the long nail portion 10 so as to allow the distal locking screw 30 to be adjusted upward or downward.

Each of the one or more distal locking screws 30 may comprise a head portion 32 and a male thread portion 34.

Each of the one or more distal locking screw holes 16 may comprise inner female threads for engaging the male thread portion 34 of the distal locking screw 30.

The long nail portion 10 may further comprise an end cap 15 configured to cap the top end option of the long nail portion 10.

The end cap 15 may comprise a male thread portion configured to engage the inner female threads of the long nail portion 10 as shown in FIGS. 1-4.

Figure 17:
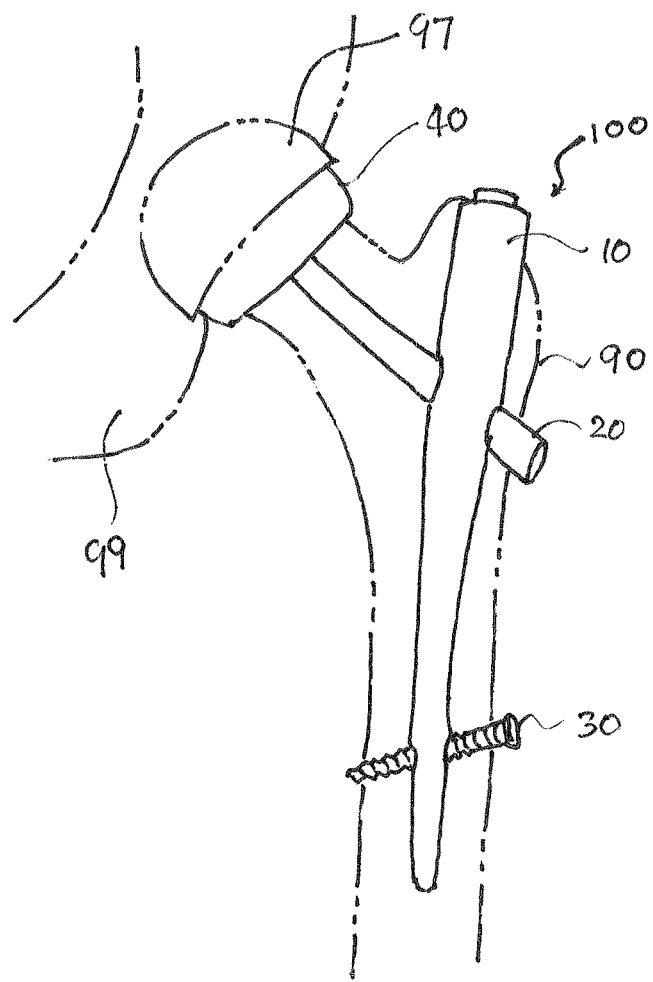
FIG. 17 is a perspective view showing a minimal invasive hip arthroplastiy device installed in a femur according to an embodiment of the present invention.

FIG. 17 shows a minimal invasive hip arthroplasty device 100 installed in a femur 90. The resurfacing head 40 engages an acetabular cup 97 embedded in the pelvis 99.

The acetabular cup 97 is fixed to the pelvis 99 by means of cement or Porocoat® porous coating.

The resurfacing head 40 may be further fixed to the head 96 of the femur 90 by means of cement or Porocoat porous coating applied to the inside 45 of the resurfacing head 40 as shown in FIG. 15.

The long nail portion 10 may be bent as shown in FIGS. 15 and 17 fitting a general shape of the femur 90.

In certain embodiments, the long nail portion 10 may meet the lag screw portion 20 by about 125 degrees. In another embodiment or for a different patient, the angle may be about 135 degrees.

The fixing pin portion 44 of the resurfacing head 40 is fixed to the resurfacing head hole 22 provided through the lag screw portion 20 by means of cement.

In FIGS. 15 and 16, exemplary dimensions are given to the parts, where the length unit is mm. The number of distal locking screws 30 depends on the length of the long nail portion 10. In the illustrated embodiment, only one distal locking screw 30 will be enough for a short one having a length of 175 mm (with a lowest tip in broken line), while two distal locking screws 30 will be needed for a longer one having a length of 235 mm.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. A durable resurfacing hip replacement device comprising:
    a long nail portion configured to be inserted into a shaft body of a femur from a top portion of the femur and disposed in the femur, wherein the long nail portion is bent slightly by a predetermined angle in a middle portion, wherein an upper part of the long nail portion is wider than a lower part of the long nail portion, wherein the long nail portion comprises a plurality of larger and smaller circular cross-sections, tapered sections and a bend and is hollow, wherein the long nail portion further comprises a set screw configured to engage threads provided inside the long nail portion;
    a lag screw portion engaging and anchoring at the long nail portion through a lag screw hole with an angle from about 110 degrees to about 140 degrees, wherein the lag screw portion is configured to be inserted into a neck of the femur; and
    a resurfacing head comprising a cup portion with an open interior configured to receive and cover a portion of a natural head, having a surface portion thereof removed such that the portion of the natural head is fitted in the open interior of the cup portion, of the femur and a fixing pin portion configured to penetrate and be inserted into the portion of the natural head and the neck of the femur and engaging the lag screw portion through a resurfacing head hole to support the cup portion,
    wherein the lag screw portion comprises:
    a support portion configured to be queued into the lag screw hole;
    a screw portion extending from the support portion;
    the resurfacing head hole provided through the screw portion; and
    a locking groove provided lengthwise along an outer surface of the support portion,
    wherein the set screw is configured to proceed along the threads provided inside the long nail portion and lock into the locking groove of the lag screw portion so as to prevent from rotating and allowing the lag screw portion to slide along the lag screw hole.

2. The durable resurfacing hip replacement device according to claim 1, wherein the lag screw hole is provided obliquely through the long nail portion.

3. The durable resurfacing hip replacement device according to claim 1, wherein the resurfacing head hole comprises inner female threads configured to engage male threads provided on the fixing pin portion.

4. The durable resurfacing hip replacement device according to claim 1, further comprising one or more distal locking screws configured to be queued through the shaft body of the femur perpendicularly and fix the long nail portion to the femur further, wherein the long nail portion further comprises one of more distal locking screw holes provided in the lower part of the long nail portion substantially perpendicularly to a direction of length of the long nail portion.

5. The durable resurfacing hip replacement device according to claim 4, wherein one of the one or more distal locking screw holes has an oblong cross-section along the direction of length of the long nail portion so as to allow the distal locking screw to be adjusted upward or downward.

6. The durable resurfacing hip replacement device according to claim 5, wherein each of the one or more distal locking screws comprises a head portion and a male thread portion.

7. The durable resurfacing hip replacement device according to claim 6, wherein each of the one or more distal locking screw holes comprises inner female threads for engaging the male thread portion of the distal locking screw.

8. The durable resurfacing hip replacement device according to claim 1, wherein the long nail portion further comprises an end cap configured to cap the top end option of the long nail portion.

9. The durable resurfacing hip replacement device according to claim 8, wherein the end cap comprises a male thread portion configured to engage the inner female threads of the long nail portion.

10. The durable resurfacing hip replacement device according to claim 1, wherein the fixing pin portion of the resurfacing head is fixed to the resurfacing head hole provided through the lag screw portion by means of adhesive or glue.

11. The durable resurfacing hip replacement device according to claim 1, wherein the fixing pin portion of the resurfacing head is fixed to the resurfacing head hole provided through the lag screw portion by means of cement.

12. The durable resurfacing hip replacement device according to claim 1, wherein the predetermined angle is determined by a general shape of the femur.

13. The durable resurfacing hip replacement device according to claim 1, wherein the resurfacing head is configured to engage an acetabular cup embedded in a portion of pelvis.

14. The durable resurfacing hip replacement device according to claim 13, wherein the acetabular cup is fixed to the pelvis by means of cement or porous coating.

* * * * *